United States Patent [19]
Abbott

[11] Patent Number: 5,425,638
[45] Date of Patent: * Jun. 20, 1995

[54] TURBINE FOR A DENTAL HANDPIECE

[76] Inventor: Phillip G. Abbott, 1750 Linda La., Maryville, Tenn. 37801

[ * ] Notice: The portion of the term of this patent subsequent to May 17, 2011 has been disclaimed.

[21] Appl. No.: 113,433

[22] Filed: Aug. 27, 1993

Related U.S. Application Data

[63] Continuation-in-part of Ser. No. 75,050, Jun. 10, 1993, Pat. No. 5,312,252.

[51] Int. Cl.⁶ ............................................. A61C 1/05
[52] U.S. Cl. ..................................... 433/132; 415/904
[58] Field of Search ............... 433/114, 116, 126, 132; 415/200, 904

[56] References Cited

U.S. PATENT DOCUMENTS

| | | | |
|---|---|---|---|
| 3,071,861 | 1/1963 | Saffir | 433/132 |
| 3,175,293 | 3/1965 | Borden | 433/132 X |
| 3,189,999 | 6/1965 | Reiter | 433/132 X |
| 3,210,848 | 10/1965 | Bizzigotti | 433/132 X |
| 3,418,715 | 12/1968 | Ellis | 433/132 X |
| 3,946,490 | 3/1976 | Sotman et al. | |
| 4,209,293 | 6/1980 | Sugai et al. | 433/132 |
| 4,244,118 | 1/1981 | Matuszak | 33/430 |
| 4,264,306 | 4/1981 | Leonard | 433/126 |
| 4,921,424 | 5/1990 | Kimura | 433/114 |
| 4,941,828 | 7/1990 | Kimura | 433/114 |
| 4,966,552 | 10/1990 | Gonser | 433/132 |
| 4,983,121 | 1/1991 | Straihammer et al. | 433/114 |
| 5,007,831 | 4/1991 | Bierbaum et al. | 433/114 |
| 5,151,325 | 9/1992 | Draskovich | 415/200 X |

OTHER PUBLICATIONS

Star Dental, Lube Free TURBINE Brochure, Division of Den-tal-ez, Inc 1991.

Primary Examiner—Nicholas D. Lucchesi
Attorney, Agent, or Firm—Pitts & Brittian

[57] ABSTRACT

A turbine for a dental handpiece. The turbine (10) includes a rotor housing (16) having at least first and second opposite end portions fabricated of a ceramic material, the rotor housing defining a cylindrical rotor chamber (18) therein. At least one inlet port (20) is provided in the rotor housing (16) for placing the rotor chamber in fluid communication with a source of pressurized fluid, and an outlet port (22) is provided for exhausting the pressurized fluid from the rotor chamber (18). The turbine (10) also includes a rotor member (24) mounted in the rotor chamber (18) of the rotor housing, the rotor member also being fabricated of a ceramic material. The rotor member (24) defines a first end portion (28) which is received through an opening (38) provided in the first end portion (28) of the rotor housing (16) for engaging and supporting a dental tool member (14). The rotor member (24) also includes a rotor disk (32) which carries a plurality of blades (34), and which is selectively rotated by the flow of pressurized fluid from the inlet port (20).

11 Claims, 6 Drawing Sheets

TURBINE FOR A DENTAL HANDPIECE

This invention is a continuation-in-part patent application based upon parent application Ser. No. 08/075,050 filed on Jun. 10, 1993, which has matured into U.S. Pat. No. 5,312,252, issued on May 17, 1994.

TECHNICAL FIELD

This invention relates to a turbine for a dental handpiece. In this particular invention the turbine includes a rotor housing fabricated of a ceramic material and a rotor member rotatably mounted therein which is also fabricated of a ceramic material.

BACKGROUND ART

Dental handpieces which incorporate pneumatic or electric turbines for selectively rotating cutting and polishing tools have been in use for many years. For example, such handpieces are disclosed in U.S. Pat. Nos. 3,946,490; 4,983,121; 4,941,828; and 4,921,424. However, in recent years concern has arisen over the possible transmission of disease through the use of non-sterile handpieces. Whereas wiping a handpiece with a disinfectant was once considered sufficient to obviate disease transmission, it is now considered an inadequate procedure, and autoclaving or chemiclaving of handpieces between patients is now recommended. However, repeated autoclaving or chemiclaving tends to damage the turbines of conventional handpieces and shorten their useful life. In this regard, modern sterilization techniques can cause rusting metal components, changes in metal tolerances, bearing cage fractures, lubricant degradation, and gasket and o-ring degradation.

Efforts have been made to design handpieces turbines which better withstand sterilization. For example, in some cases the turbines of the handpiece have been provided with ceramic ball bearings to increase bearing life and obviate the need for the use of a lubricant. Further, in some cases heat resistant O-rings are being used. For example, the 430 SWL handpiece manufactured by Star Dental, a division of Den-Tal-Ez, Inc. of Lancaster, Penna., incorporates such features. However, such features offer only a partial solution to the problem.

Therefore, it is an object of the present invention to provide a turbine for a dental handpiece which can withstand repeated autoclaving or chemiclaving.

It is another object of the present invention to provide a dental handpiece which does not require the use of ball bearings or lubricants.

Yet another object of the present invention is to provide a dental handpiece which is lightweight, yet durable.

Still another object of the present invention is to provide a dental handpiece which is inexpensive to manufacture and maintain.

DISCLOSURE OF THE INVENTION

Other objects and advantages will be accomplished by the present invention which provides a turbine for a dental handpiece. The turbine includes a rotor housing having at least first and second opposite end portions which are fabricated of a ceramic material, the rotor housing defining a cylindrical rotor chamber therein. At least one inlet port is provided in the rotor housing for placing the rotor chamber in fluid communication with a source of pressurized air or other fluid, and an outlet port is provided for exhausting the pressurized air or fluid from the rotor chamber. The turbine also includes a rotor member rotatably mounted in the rotor chamber of the rotor housing, the rotor member also being fabricated of a ceramic material. The rotor member includes a shaft portion which defines a first end portion which is received through a rotor shaft opening provided in the rotor housing. The first end portion of the shaft portion of the rotor member serves to engage and rotatably support a cutting or polishing tool. The rotor member also includes a rotor disk which carries a plurality of blade members, the rotor disk being rotatably positioned within the rotor chamber proximate the inlet port and the outlet port so as to be selectively rotated by the flow of pressurized fluid injected through the inlet port.

BRIEF DESCRIPTION OF THE DRAWINGS

The above mentioned features of the invention will be more clearly understood from the following detailed description of the invention read together with the drawings in which.

BEST MODE FOR CARRYING OUT THE INVENTION

Figures 3, 4:
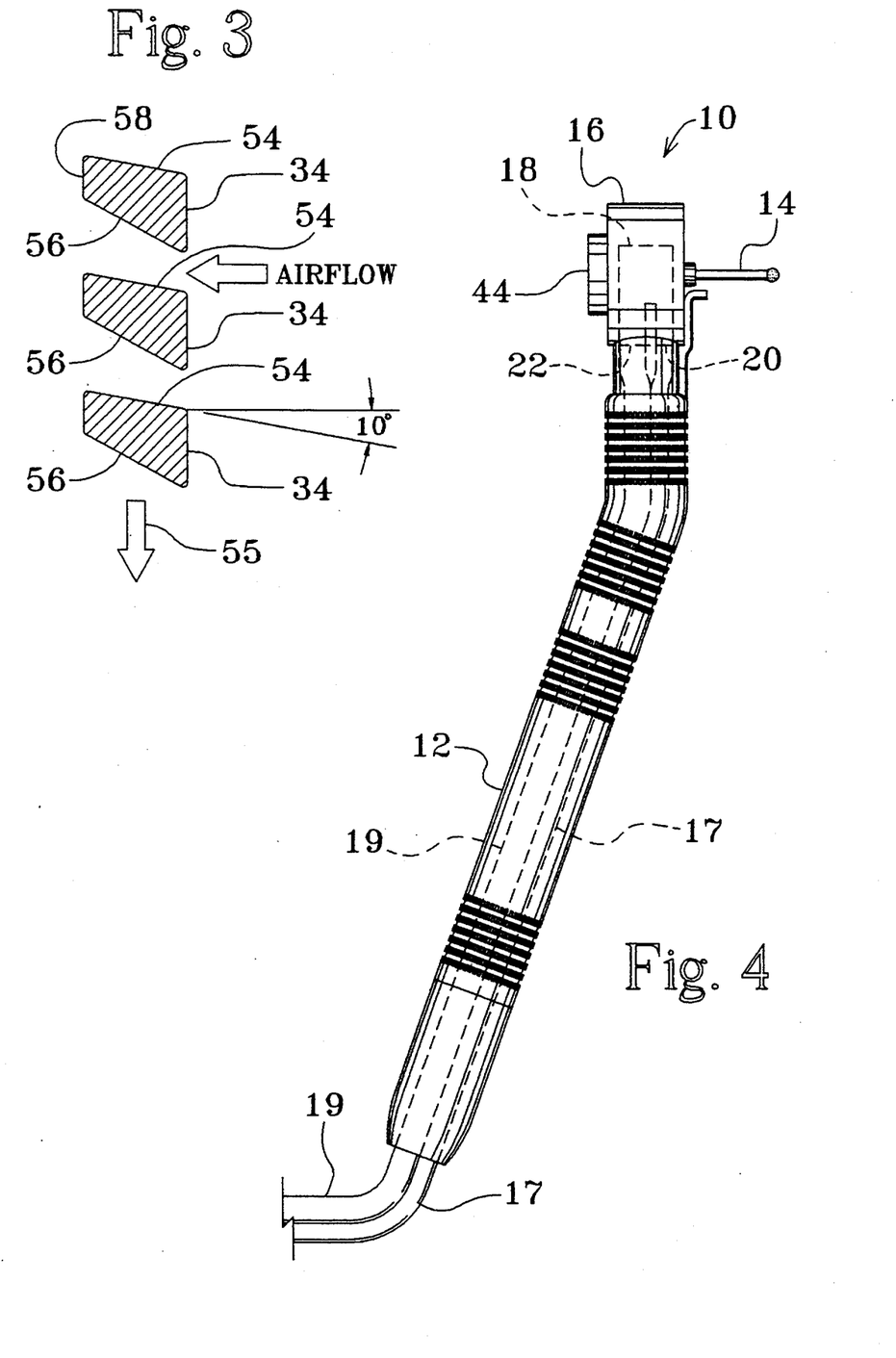
FIG. 3 illustrates a diagrammatic side elevation view of the blades of the rotor member of a turbine of the present invention.
FIG. 4 illustrates a side elevation view of a dental handpiece incorporating a turbine of the present invention.

A turbine for a dental handpiece incorporating various feature of the present invention is illustrated generally at 10 in the Figures. As illustrated in FIG. 4, the turbine 10 is designed to be supported on a handle 12, the turbine 10 and the handle 12 comprising a dental handpiece. The turbine 10 is designed to selectively rotate various tool members used in dental procedures, such as, for example, the illustrated tool member 14. As will be discussed in detail below the turbine 10 is driven by air, or other fluid, under pressure supplied by a suitable source of pressurized fluid (not shown), such as a compressor.

The turbine 10 includes a rotor housing 16 fabricated of a ceramic material. In one preferred embodiment the ceramic material is a high density aluminum oxide ceramic, such as SP 99.9 manufactured by Speceram. However, there are other high density ceramic materials which may be suitable, and the high density aluminum oxide ceramic referenced herein is merely illustrative of one suitable ceramic fabricating material. The housing 16 is typically cylindrical in shape and defines a cylindrical rotor chamber 18. An inlet port 20 is provided in the housing 16 for placing the rotor chamber 18 in fluid communication with the source of pressurized fluid, and an outlet port 22 is provided for exhausting fluid from the chamber 18. As illustrated in FIG. 4, the inlet port 20 can be connected to a suitable source of pressurized fluid with a supply conduit 17 which extends through the handle 12, and, similarly, an exhaust conduit 19, which communicates with the outlet port 22 and extends through the handle 12, can be provided in order to facilitate the exhausting of fluid from the handpiece.

Figure 1:
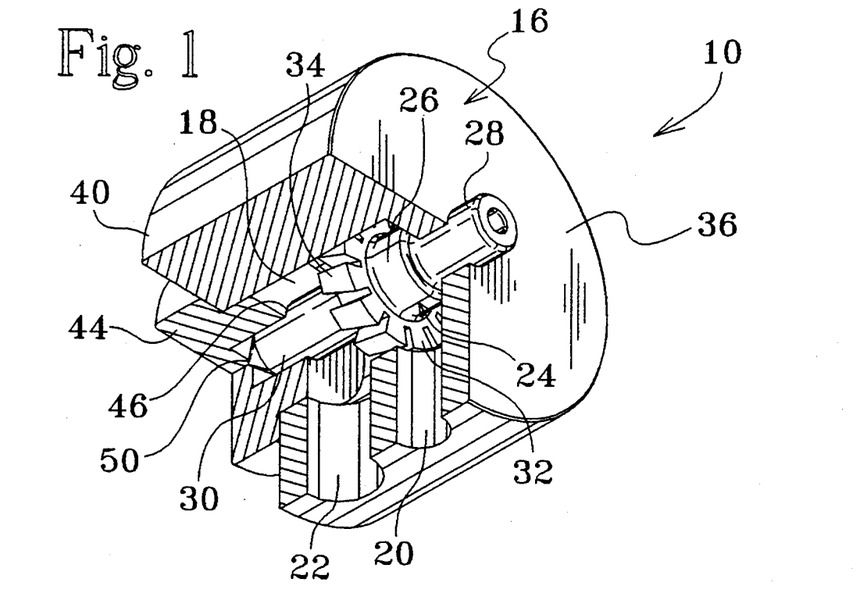
FIG. 1 illustrates a perspective view, partially in section, of a turbine of the present invention.
Figure 2:
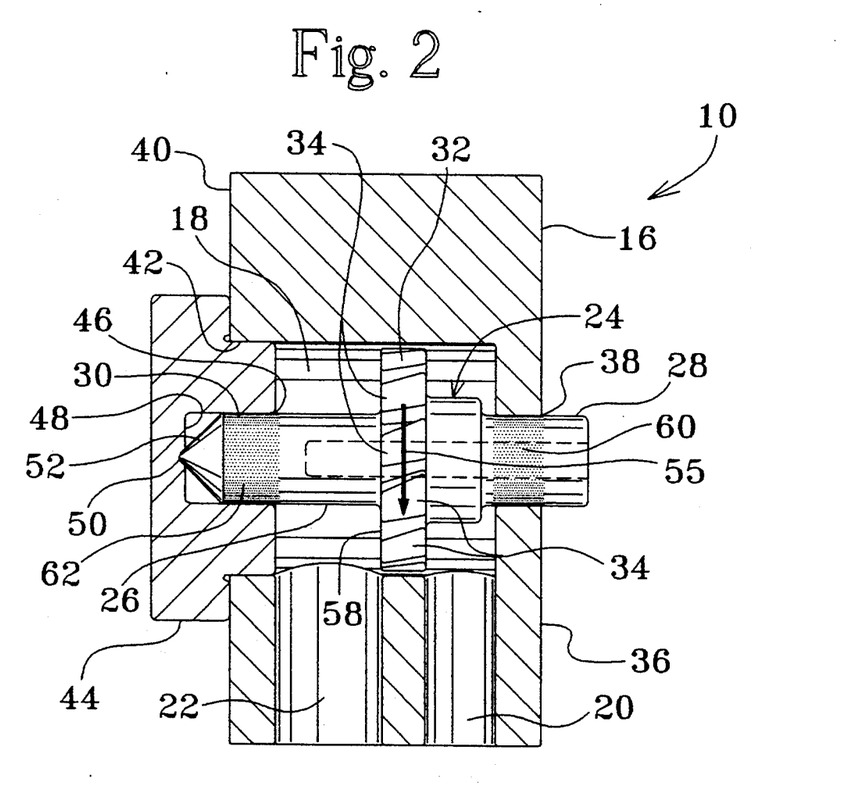
FIG. 2 illustrates a side elevation view, in section, of a turbine of the present invention.

As best illustrated in FIGS. 1 and 2, a rotor member 24 is rotatably mounted in the rotor chamber 18 of the housing 16. The rotor member 24 is also fabricated of a ceramic material, which in the preferred embodiment is a high density aluminum oxide ceramic as discussed above. The rotor member 24 includes a shaft portion 26 defining first and second end portions 28 and 30, respectively, and a rotor disk 32 provided with a plurality of radially disposed blades 34.

With respect to the rotational support of the rotor member 24 within the housing 16, in the preferred illustrated embodiment the rotor housing 16 defines a first end portion 36 which is provided with an opening 38 through which the first end portion 28 of the shaft portion 26 is received such that the outboard end of the first end portion 28 is exterior to the housing 16. The rotor housing 16 also defines a second end portion 40 which is provided with a further opening 42, and the rotor housing 16 includes a removable cap member 44 which is received in such further opening 42 so as to define the rear wall of the housing 16. The cap member 44 is also fabricated of a ceramic material, which in the preferred embodiment is a high density aluminum oxide ceramic as discussed above.

The cap member 44 is provided with an annular receptor 46 which rotatably receives the second end portion 30 of the shaft portion 26 of the rotor member 24. The receptor 46 defines an end wall 48 which is provided with a centrally disposed indentation 50 receptive of the second end portion 30 of the shaft portion 26. In this regard, the second end portion 30 of the shaft portion 26 has a conical end 52, at least the outboard portion of which is rotatably received in the indentation 50 of the receptor 46 to facilitate supporting the rotor member 24 in the desired coaxial position within the rotor chamber 18.

The fabrication of the rotor housing 16, the cap member 44 and the rotor member 24 from high density ceramics provides the turbine 10 with great advantages over the prior art turbines which utilize conventional metal fabricating materials. In this regard, aluminum oxide ceramics are light weight, yet have high friction, abrasion and compression strengths, and are corrosion and heat-resistant. Thus, the use of a ceramic fabricating material provides greater durability and less susceptibility to ware. Also, with such high density ceramic materials there is less expansion and contraction of the material due to changes in temperature than is the case with conventional metal fabricating materials, and being constructed of a high density ceramic material, the components of the turbine 10 are less susceptible to damage as a result of repetitive autoclaving and/or chemiclaving.

With respect to the operation of the turbine 10, it will be noted that when the rotor member 24 is rotatably journalled in the opening 38 and the receptor 46, with the outboard portion of the conical end 52 in the indentation 50, the rotor disk 32 is disposed in the chamber 18 between the inlet port 20 and the outlet port 22 so as to utilize the kinetic energy of the flow of fluid through the chamber 18. In this regard, the blades 34 are selectively pitched such that the flow of fluid through the chamber 1e produces rotation of the rotor member 24 in the direction of the arrow 55. Of course, such rotation of the rotor member 24 results in the desired rotation of the tool member 14 mounted in the first end portion 28 of the rotor member 24.

More specifically, and as best illustrated in FIG. 3, in the preferred embodiment each blade 34 defines a trailing face 54 which is oriented at approximately a ten degree (10°) angle relative to the rotational axis of rotor member 24 and the airflow in the chamber 18. Also, each blade 34 defines a leading face 56 which is oriented at a selected greater angle relative to the rotational axis of rotor member 24 than the angle of the trailing face 54, such that the space between the blades 34 widens toward the low pressure surface 58 of the rotor member 24 to facilitate efficient fluid flow through the rotor member 24. Of course, the illustrated rotor blade configuration simply constitutes one preferred configuration and other blade configurations may be used to produce the desire rotation.

It will be recognized by those skilled in the art that the use of a high density ceramic fabricating material for the housing 16, the rotor member 24 and the cap member 44 obviates the need for mechanical bearings between the rotor member 24 and the housing 16 or between the rotor member 24 and cap member 44. As noted above, the ceramic material is light weight and ware resistant. However, in order to facilitate the free rotation of the rotor member 24 in the rotor housing 16, in the preferred embodiment the first end portion 28 of the shaft portion 26 defines a polished bearing surface portion 60 (see FIG. 2) proximate the point where the first end portion 28 is received through the opening 38. Similarly, a further polished bearing surface portion 62 is provided on the second end portion 30 of the shaft portion 26 proximate the point where the second end portion 30 is received in the annular receptor 46 of the cap member 44.

Further, it will be noted that the inlet port 20 and the outlet port 22 are disposed such that fluid flow through the rotor chamber 18 in the proximity of the rotor disk 32 is in the direction of the cap member 44 or rear wall of the housing 16. As a result, the fluid flow biases the rotor member 24 in the direction of the cap member 44 such that during operation the outboard portion of the conical end 52 of the rotor member remains seated in the indentation 50 so as to maintaining the desire coaxial position of the rotor member 24 within the rotor chamber 18. As a result friction between the rotor member 24 and the housing 16 and cap member 44 is minimized.

Figure 5:
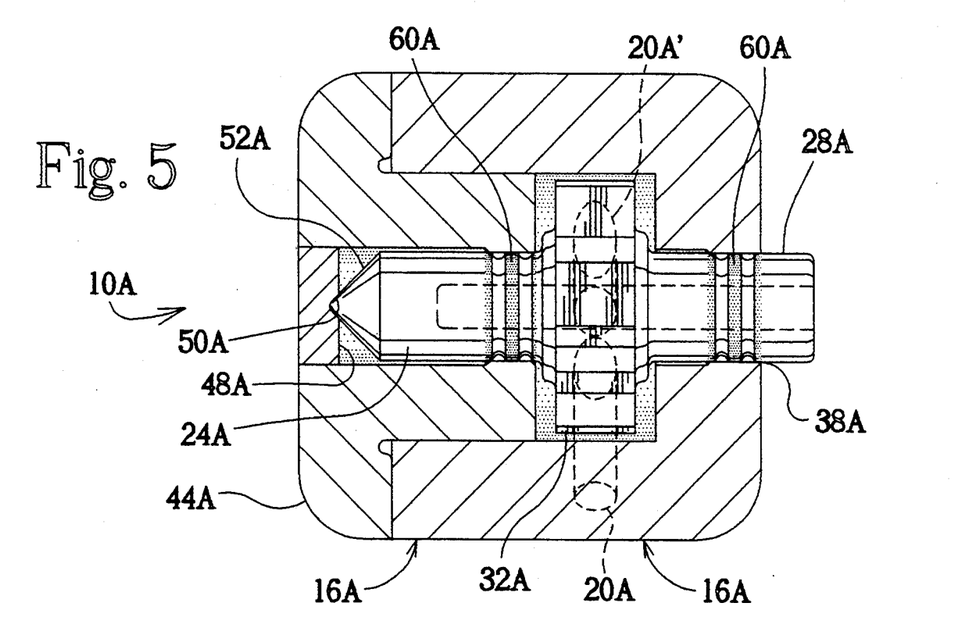
FIG. 5 illustrates a side elevation view, in section at 5—5 of FIG. 6, of an alternate embodiment of the turbine of the present invention.
Figure 6:
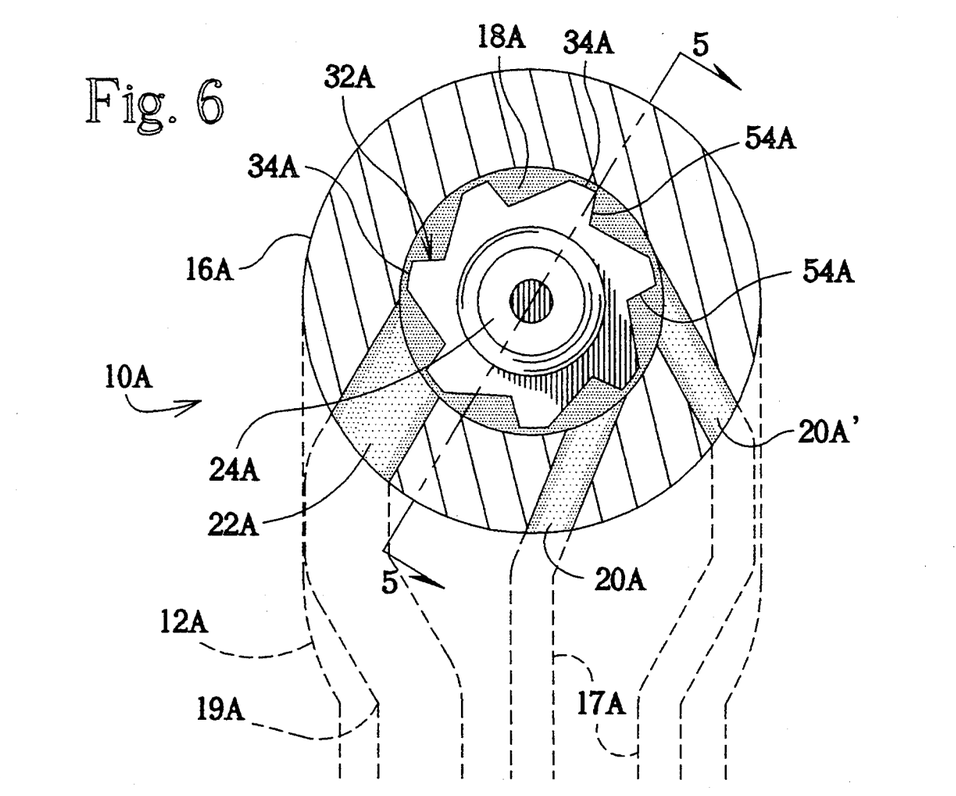
FIG. 6 illustrates an end view, partially in section, of an alternate embodiment of the turbine of the present invention.
Figure 7:
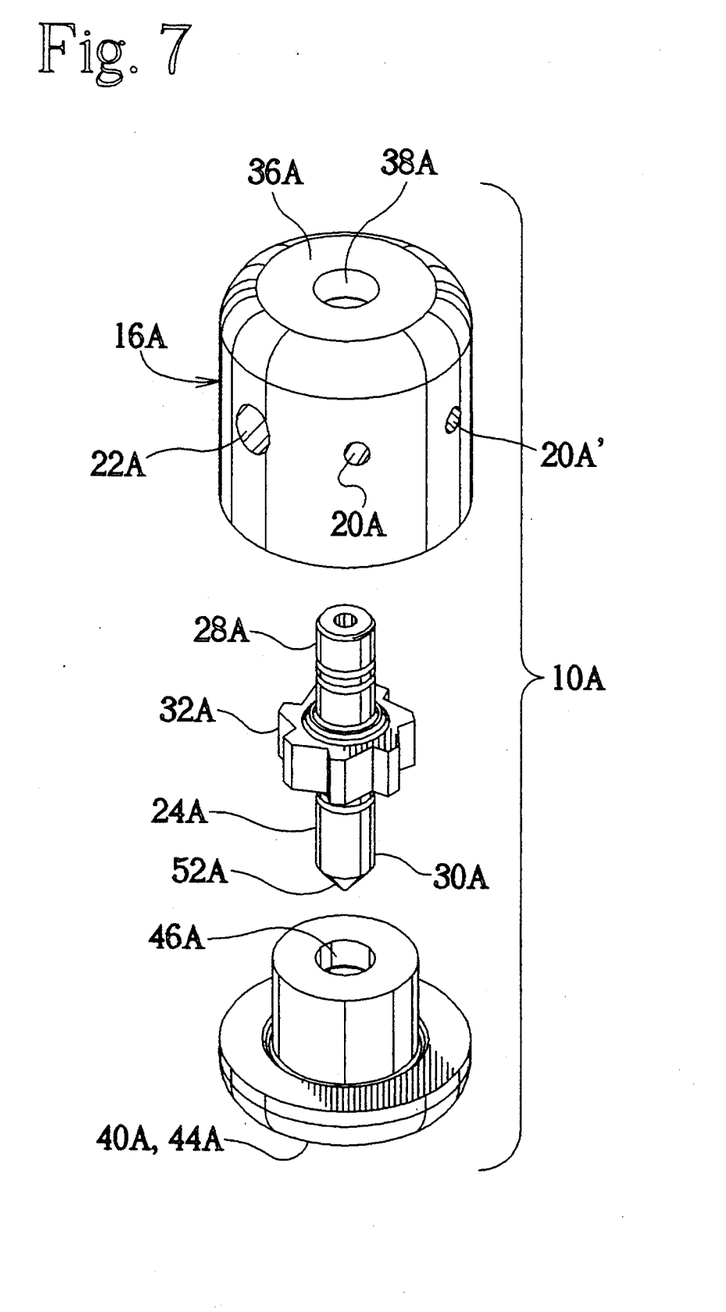
FIG. 7 illustrates an exploded perspective view of an alternate embodiment of the turbine of the present invention.

In FIGS. 5, 6 and 7, an alternate embodiment of the turbine of the present invention is illustrated generally at 10A. For convenience, features and components of the turbine 10A which are common to the above-described turbine 10 are referenced with common numeral followed by the alphabetic character "A".

As in the case of the turbine 10, the rotor housing 16A, the rotor member 24A, and cap member 44A, of the turbine 10A are fabricated of a ceramic material. However, the rotor member 24A of the turbine 10A incorporates a different rotor disk configuration. In this regard, each of the blades 34A defines a trailing face 54A which is aligned in a plane substantially parallel to the rotational axis of the rotor member 24A such that the rotor disk 32A defines a paddle wheel configuration. It will be noted, however, that whereas the trailing faces 54A are aligned substantially parallel to the axis of the rotor member 24A, it is contemplated that the faces 54A themselves may define concave surfaces or other irregular surfaces, rather than the planar surfaces illustrated.

The rotor housing 16A is provided with at least one, and preferably two, inlet ports 20A and 20A$^1$ to inject fluid under pressure into the rotor chamber 18A proximate the rotor disk 32A. In this regard, the inlet ports 20A and 20A$^1$ are aligned such that the air injected into the chamber 18A is directed toward the trailing faces 54A of the blades 34A to effect rotation of the rotor member 24A. Air injected into the chamber 18A is exhausted through the outlet port 22A. It will be noted that by providing two inlet ports 20A and 20A$^1$ air injected into the chamber 18A can act upon two trailing faces 54A simultaneously to facilitate rotation of the rotor member 24A, but it will be understood that a single inlet port could be used.

Figure 8:
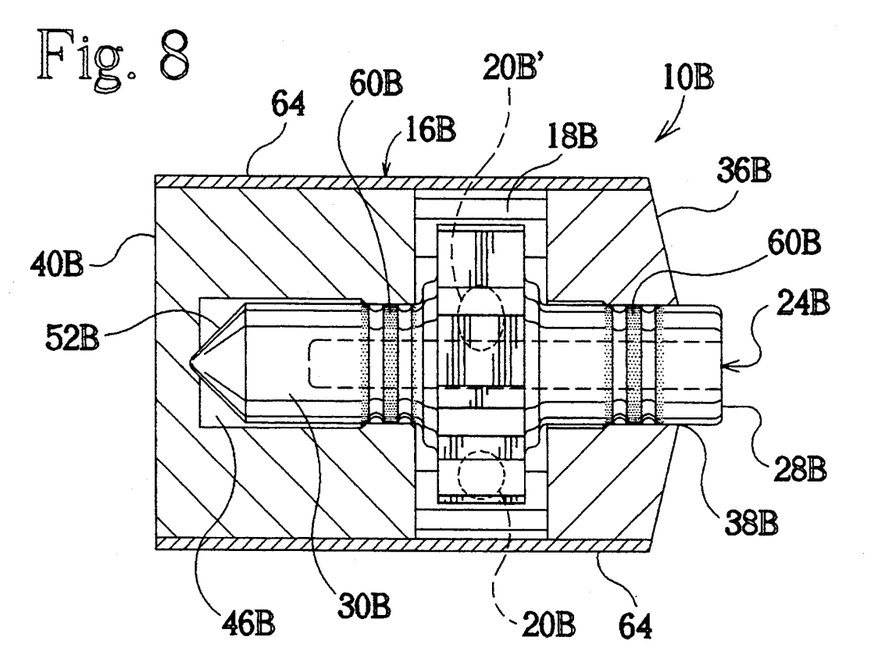
FIG. 8 illustrates a side elevation view, in section at 8—8 of FIG. 9, of a further alternate embodiment of the turbine of the present invention.
Figure 9:
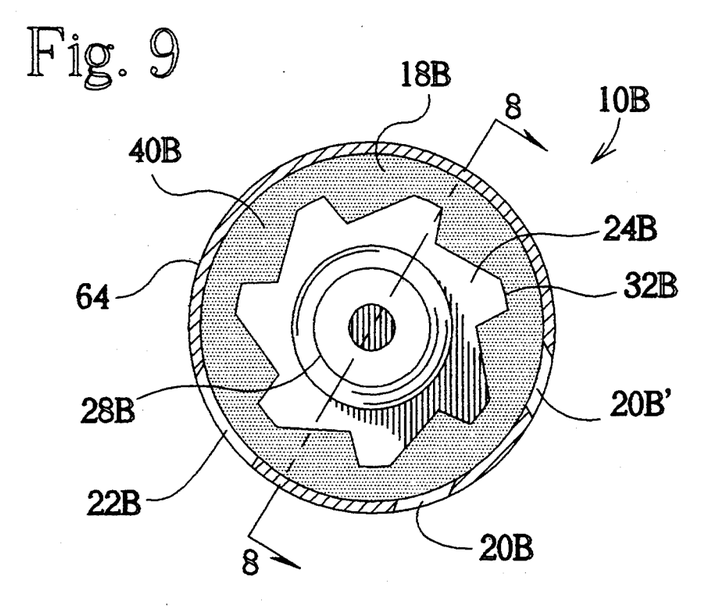
FIG. 9 illustrates an end view, partially in section, of a further alternate embodiment of the turbine of the present invention.
Figure 10:
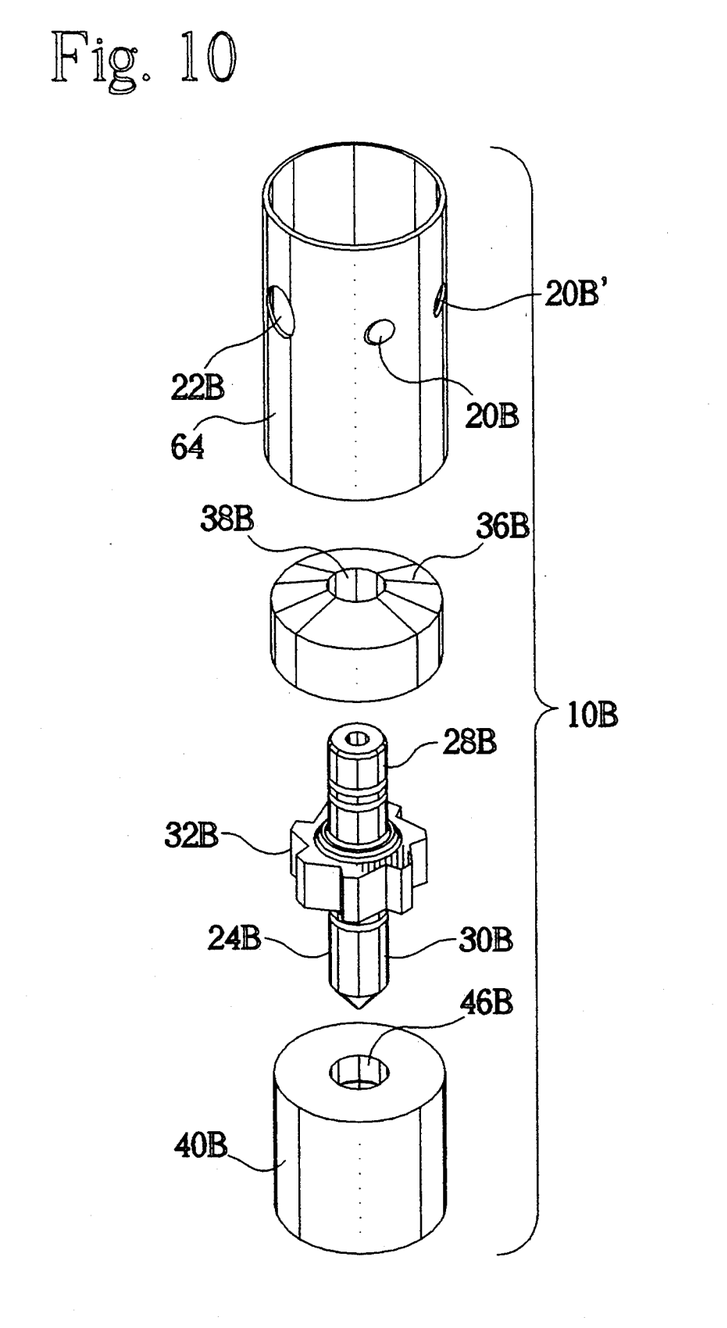
FIG. 10 illustrates an exploded perspective view of a further alternate embodiment of the turbine of the present invention.

In FIGS. 8, 9 and 10, a further alternate embodiment of the turbine of the present invention is illustrated generally at 10B. For convenience, features and components of the turbine 10B which are common to the above-described turbines 10 and 10A are referenced with common numeral followed by the alphabetic character "B".

In the turbine 10B the rotor housing 16B includes first end portion 36B defining the opening 38B for rotatably receiving the first end portion 28B of the rotor member 24B, and a separate, second end portion 40B which defines the receptor 46B for rotatably receiving the second end portion 30B of the rotor member 24B. The first end portion 36B and second end portion 40B are disposed within an outer housing 64 and are selectively spaced to accommodate the rotor disk 32B therebetween. Thus, as best illustrated in FIG. 8, the first end portion 36B and second end portion 40B, and the outer housing 64, cooperatively, define the rotor chamber 18B.

The first end portion 36B and second end portion 40B are fabricated of a ceramic material, as discussed above with respect to the rotor housing 16. However, the outer housing 64 can be fabricated of metal or other material since the housing 64 is not in rotational contact with the rotor member 24B. In this regard, the first end portion 36B and second end portion 40B serve essentially as ceramic bushings to rotatably support the ceramic rotor member 24B, thereby obviating the need for mechanical bearings and ensuring the durability of the primary operative components of the turbine.

In light of the above it will be recognized that the present invention provides a turbine for a dental handpiece having great advantages over the prior art. Since the various components of the turbine 10, 10A and 10B are fabricated of a high density ceramic, the turbine is light weight, yet durable and can withstand repeated autoclaving and chemiclaving. The construction of the turbine obviates the need for ball bearings which are susceptible to damage from repeated autoclaving or chemiclaving, and obviates the need for lubricants which tend to degrade as a result of repeated sterilizations. However, while a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. A turbine for a dental handpiece for selectively rotating a tool member, said turbine comprising:
   a rotor housing having a first end portion and a second end portion, at least said first and second end portions of said rotor housing being fabricated of a ceramic material, said rotor housing defining a rotor chamber and being provided with at least one inlet port for placing said rotor chamber in fluid communication with a source of pressurized fluid whereby pressurized fluid is selectively injected into said rotor chamber, and with an outlet port for exhausting said pressurized fluid from said rotor chamber, said first end portion of said rotor housing being provided with a rotor shaft opening communicating with said rotor chamber; and
   a rotor member rotatably mounted in said rotor chamber of said rotor housing, said rotor member being fabricated of a ceramic material, said rotor member including a shaft portion defining a first end portion received through said rotor shaft opening of said first end portion of said rotor housing for engaging and supporting said tool member, said rotor member also including a rotor disk carrying a plurality of blade members, said rotor disk being rotatably positioned within said rotor chamber so as to be selectively rotated by the flow of said pressurized fluid from said inlet port of said rotor housing.

2. The turbine of claim 1 wherein said ceramic material of which said first and second end portions of said rotor housing and said rotor member are fabricated comprises an aluminum oxide ceramic.

3. The turbine of claim 1 wherein said rotor chamber is cylindrical and said rotor shaft opening is coaxially disposed in said first end portion of said rotor housing, said rotor housing being provided with a further opening in said second end of said housing communicating with said rotor chamber, and wherein said rotor housing includes a cap member for being received in said further opening of said rotor housing, said cap member being fabricated of a ceramic material.

4. The turbine of claim 3 wherein said cap member is provided with an annular receptor having an end wall defining a coaxial indentation, and wherein said rotor member defines a second end portion having a conical outboard end, at least a portion of which is rotatably received in said indentation of said annular receptor of said cap member.

5. The turbine of claim 4 wherein said ceramic material of which said first and second end portions of said rotor housing, said rotor member and said cap Member are fabricated comprises an aluminum oxide ceramic material.

6. The turbine of claim 1 wherein said rotor chamber is cylindrical and said rotor shaft opening is coaxially disposed in said first end portion of said rotor housing, said rotor chamber defining a rear wall provided with an annular receptor having an end wall defining an indentation, and wherein said rotor member defines a second end portion having a conical outboard end, at least a portion of which is rotatably received in said indentation of said annular receptor.

7. The turbine of claim 6 wherein said ceramic material of which said first and second end portions of said rotor housing and said rotor member are fabricated comprises an aluminum oxide ceramic.

8. A turbine for a dental handpiece for selectively rotating a tool member, said turbine comprising:
  a rotor housing fabricated of an aluminum oxide ceramic material, said rotor housing defining a cylindrical rotor chamber and being provided with a pair of inlet ports for placing said rotor chamber in fluid communication with a source of pressurized fluid whereby pressurized fluid is selectively injected into said rotor chamber, and with an outlet port for exhausting said pressurized fluid from said rotor chamber, said rotor housing being provided with a rotor shaft opening at a first end of said rotor housing communicating with said rotor chamber and a further opening at a second end of said housing communicating with said rotor chamber;
  a cap member for being received in said further opening of said rotor housing, said cap member being fabricated of an aluminum oxide ceramic, said cap member defining an annular receptor defining an end wall provided with a coaxial indentation; and
  a rotor member rotatably mounted in said rotor chamber of said rotor housing, said rotor member being fabricated of an aluminum oxide ceramic material, said rotor member including a shaft portion defining a first end portion received through said rotor shaft opening of said rotor housing for engaging and supporting the tool member, and defining a second end portion having a conical outboard end, at least a portion of which is rotatably received in said indentation of said annular receptor of said cap member, said rotor member also including a rotor disk carrying a plurality of blade members, said rotor disk being rotatably positioned within said rotor chamber proximate said inlet ports and said outlet port so as to be selectively rotated by said pressurized fluid injected into said rotor chamber through said inlet ports of said rotor housing.

9. A dental handpiece for selectively rotating a tool member, said dental handpiece comprising a handle provided with at least one supply conduit for placing said handpiece in fluid communication with a source of pressurized fluid, and comprising a turbine mounted on said handle, said turbine including:
  a rotor housing fabricated of a ceramic material, said rotor housing defining a rotor chamber and being provided with at least one inlet port for placing said rotor chamber in fluid communication with said supply conduit whereby pressurized fluid is selectively injected into said rotor chamber, and with an outlet port for exhausting said pressurized fluid from said rotor chamber, said rotor housing being provided with a rotor shaft opening communicating with said rotor chamber; and
  a rotor member rotatably mounted in said rotor chamber of said rotor housing, said rotor member being fabricated of a ceramic material, said rotor member including a shaft portion defining a first end portion received through said rotor shaft opening of said rotor housing for engaging and supporting said tool member, said rotor member also including a rotor disk carrying a plurality of blade members, said rotor disk being rotatably positioned within said rotor chamber so as to be selectively rotated by the flow of said pressurized fluid from said inlet port of said rotor housing.

10. A dental handpiece for selectively rotating a tool member, said dental handpiece comprising a handle provided with at least one supply conduit for placing said handpiece in fluid communication with a source of pressurized fluid, and comprising a turbine, said turbine including:
  a rotor housing fabricated of an aluminum oxide ceramic material, said rotor housing defining a cylindrical rotor chamber and being provided with at least one inlet port for placing said rotor chamber in fluid communication with said supply conduit whereby pressurized fluid is selectively injected into said rotor chamber, and with an outlet port for exhausting said pressurized fluid from said rotor chamber, said rotor housing being provided with a rotor shaft opening at a first end of said rotor housing communicating with said rotor chamber and a further opening at a second end of said housing communicating with said rotor chamber;
  a cap member for being received in said further opening of said rotor housing, said cap member being fabricated of an aluminum oxide ceramic, said cap member defining an annular receptor defining an end wall provided with a coaxial indentation; and
  a rotor member rotatably mounted in said rotor chamber of said rotor housing, said rotor member being fabricated of an aluminum oxide ceramic material, said rotor member including a shaft portion defining a first end portion received through said rotor shaft opening of said rotor housing for engaging and supporting the tool member, and defining a second end portion having a conical outboard end, at least a portion of which is rotatably received in said indentation of said annular receptor of said cap member, said rotor member also including a rotor disk carrying a plurality of blade members, said rotor disk being rotatably positioned within said rotor chamber proximate said inlet port and said outlet port so as to be selectively rotated by said pressurized fluid injected into said rotor chamber through said inlet port of said rotor housing.

11. A turbine for a dental handpiece for selectively rotating a tool member, said turbine comprising:
  a rotor housing having a first end portion and a second end portion and having an outer housing for securing said first and second end portions of said rotor housing in a selectively spaced disposition, said first and second end portions of said rotor housing being fabricated of a ceramic material, said rotor housing defining a rotor chamber and being provided with at least one inlet port for placing said rotor chamber in fluid communication with a source of pressurized fluid whereby pressurized fluid is selectively injected into said rotor chamber, and with an outlet port for exhausting said pressurized fluid from said rotor chamber, said first end portion of said rotor housing being provided with a rotor shaft opening communicating with said rotor chamber; and
  a rotor member rotatably mounted in said rotor chamber of said rotor housing, said rotor member being fabricated of a ceramic material, said rotor member including a shaft portion defining a first end portion received through said rotor shaft opening of said first end portion of said rotor housing for engaging and supporting said tool member, said rotor member also including a rotor disk carrying a plurality of blade members, said rotor disk being rotatably positioned within said rotor chamber so as to be selectively rotated by the flow of said pressurized fluid from said inlet port of said rotor housing.

* * * * *